United States Patent
Rule et al.

(10) Patent No.: US 6,959,211 B2
(45) Date of Patent: Oct. 25, 2005

(54) DEVICE FOR CAPTURING THERMAL SPECTRA FROM TISSUE

(75) Inventors: Peter Rule, Los Altos Hills, CA (US); James R. Braig, Piedmont, CA (US); Daniel S. Goldberger, Boulder, CO (US); Julian M. Cortella, Alameda, CA (US); Heidi M. Smith, Union City, CA (US); Roger O. Herrera, Emeryville, CA (US); Kenneth G. Witte, San Jose, CA (US); Philip C. Hartstein, Cupertino, CA (US); Mark D. Agostino, Alameda, CA (US)

(73) Assignee: OptiScan Biomedical Corp., Alameda, CA (US)

( * ) Notice: Subject to any disclaimer, the term of this patent is extended or adjusted under 35 U.S.C. 154(b) by 191 days.

(21) Appl. No.: 10/213,730

(22) Filed: Aug. 6, 2002

(65) Prior Publication Data

Related U.S. Application Data

(63) Continuation-in-part of application No. 09/760,423, filed on Jan. 11, 2001, now Pat. No. 6,636,753, which is a continuation of application No. 09/265,195, filed on Mar. 10, 1999, now Pat. No. 6,198,949.

(60) Provisional application No. 60/310,898, filed on Aug. 8, 2001.

(51) Int. Cl.$^7$ ............................................. A61B 5/00
(52) U.S. Cl. ...................................... 600/310; 600/316
(58) Field of Search ............................ 600/322, 316, 600/473, 476, 344, 334, 310

(56) References Cited

U.S. PATENT DOCUMENTS 4,223,680 A    9/1980  Jöbsis
4,380,240 A  *  4/1983  Jobsis et al. ................ 600/344
4,798,955 A    1/1989  Rosenthal
4,834,802 A    5/1989  Prier
4,926,867 A    5/1990  Kanda et al.
4,953,552 A    9/1990  DeMarzo
5,028,787 A    7/1991  Rosenthal et al.
5,035,243 A    7/1991  Muz
5,111,817 A    5/1992  Clark et al.
5,131,391 A  *  7/1992  Sakai et al. ................ 600/334

(Continued)

FOREIGN PATENT DOCUMENTS

WO    WO 99/55222    11/1999

(Continued)

Primary Examiner—Eric F. Winakur
Assistant Examiner—Matthew Kremer
(74) Attorney, Agent, or Firm—Knobbe Martens Olson & Bear LLP (57) ABSTRACT

A device and method are provided for use with a noninvasive optical measurement system, such as a thermal gradient spectrometer, for improved determination of analyte concentrations within living tissue. In one embodiment, a wearable window is secured to a patient's forearm thereby isolating a measurement site on the patient's skin for determination of blood glucose levels. The wearable window effectively replaces a window of the spectrometer, and thus forms an interface between the patient's skin and a thermal mass window of the spectrometer. When the spectrometer must be temporarily removed from the patient's skin, such as to allow the patient mobility, the wearable window is left secured to the forearm so as to maintain a consistent measurement site on the skin. When the spectrometer is later reattached to the patient, the wearable window will again form an interface between the spectrometer and the same location of skin as before.

40 Claims, 6 Drawing Sheets

U.S. PATENT DOCUMENTS

| | | | | |
|---|---|---|---|---|
| 5,140,985 A | | 8/1992 | Schroeder et al. | |
| 5,211,160 A | | 5/1993 | Talish et al. | |
| 5,370,114 A | | 12/1994 | Wong et al. | |
| 5,419,321 A | | 5/1995 | Evans | |
| 5,482,034 A | | 1/1996 | Lewis et al. | |
| 5,492,118 A | | 2/1996 | Gratton et al. | |
| 5,515,847 A | | 5/1996 | Braig et al. | |
| 5,615,672 A | | 4/1997 | Braig et al. | |
| 5,642,733 A | | 7/1997 | Archibald et al. | |
| 5,771,890 A | | 6/1998 | Tamada | |
| 5,817,010 A | * | 10/1998 | Hibl | 600/344 |
| 5,823,951 A | | 10/1998 | Messerschmidt | |
| 5,827,183 A | | 10/1998 | Kurnik et al. | |
| 5,879,373 A | | 3/1999 | Röper et al. | |
| 5,900,632 A | | 5/1999 | Sterling et al. | |
| 5,991,648 A | | 11/1999 | Levin | |
| 6,016,435 A | | 1/2000 | Maruo et al. | |
| 6,023,629 A | | 2/2000 | Tamada | |
| 6,025,597 A | | 2/2000 | Sterling et al. | |
| 6,048,323 A | | 4/2000 | Hon | |
| 6,072,180 A | | 6/2000 | Kramer et al. | |
| 6,073,038 A | | 6/2000 | Wang et al. | |
| 6,161,028 A | | 12/2000 | Braig et al. | |
| 6,175,752 B1 | | 1/2001 | Say et al. | |
| 6,198,949 B1 | * | 3/2001 | Braig et al. | 600/310 |
| 6,240,306 B1 | | 5/2001 | Rohrscheib et al. | |
| 6,241,663 B1 | | 6/2001 | Wu et al. | |
| 6,264,622 B1 | | 7/2001 | Augustine | |
| 6,381,489 B1 | * | 4/2002 | Ashibe | 600/344 |
| 6,577,885 B1 | | 6/2003 | Braig et al. | |
| 6,631,282 B2 | | 10/2003 | Rule et al. | |
| 6,633,771 B1 | | 10/2003 | Braig et al. | |
| 6,636,753 B1 | | 10/2003 | Braig et al. | |
| 2003/0122081 A1 | | 7/2003 | Herrera et al. | |

FOREIGN PATENT DOCUMENTS

WO      WO 01/30236      5/2001

* cited by examiner

DEVICE FOR CAPTURING THERMAL SPECTRA FROM TISSUE

RELATED APPLICATIONS

This application claims the benefit of U.S. Provisional Patent Application No. 60/310,898, filed Aug. 8, 2001, entitled DEVICE FOR CAPTURING THERMAL SPECTRA FROM TISSUE, the entire contents of which are hereby incorporated by reference herein and made a part of this specification. In addition, this application is a continuation-in-part of U.S. patent application Ser. No. 09/760,423, filed Jan. 11, 2001, now U.S. Pat. No. 6,636,753, issued Oct. 21, 2003, titled SOLID-STATE NON-INVASIVE INFRARED ABSORPTION SPECTROMETER FOR THE GENERATION AND CAPTURE OF THERMAL GRADIENT SPECTRA FROM LIVING TISSUE, which is a continuation of U.S. patent application Ser. No. 09/265,195, filed Mar. 10, 1999, now U.S. Pat. No. 6,198,949, issued Mar, 6, 2001, titled SOLID-STATE NON-INVASIVE INFRARED ABSORPTION SPECTROMETER FOR THE GENERATION AND CAPTURE OF THERMAL GRADIENT SPECTRA FROM LIVING TISSUE.

BACKGROUND OF THE INVENTION

1. Field of the Invention

This invention relates generally to determining analyte concentrations within living tissue. More particularly, this invention relates to a device for attaching a portable window to living tissue for consistent transfer of thermal spectra to and from the tissue.

2. Description of the Related Art

Millions of diabetics are forced to draw blood on a daily basis to determine their blood glucose levels. A search for a noninvasive methodology to accurately determine blood glucose levels has been substantially expanded in order to alleviate the discomfort of these individuals. A significant advance in the state of the art of noninvasive blood glucose analysis has been realized by an apparatus taught in U.S. Pat. No. 6,198,949, titled SOLD-STATE NON-INVASIVE INFRARED ABSORPTION SPECTROMETER FOR THE GENERATION AND CAPTURE OF THERMAL GRADIENT SPECTRA FROM LIVING TISSUE, issued Mar. 6, 2001, and by methodology taught in U.S. Pat. No. 6,161,028, titled METHOD FOR DETERMINING ANALYTE CONCENTRATION USING PERIODIC TEMPERATURE MODULATION AND PHASE DETECTION, issued Dec. 12, 2000, as well as the methods and apparatus taught in the Assignee's U.S. Pat. No. 6,580,934, entitled METHOD AND APPARATUS FOR DETERMINING ANALYTE CONCENTRATION USING PHASE AND MAGNITUDE DETECTION OF A RADIATION TRANSFER FUNCTION, issued Jun. 17, 2003. The entire contents of each of the above-mentioned patents and of the above-mentioned patent application are hereby incorporated by reference herein.

SUMMARY OF THE INVENTION

Although the above-mentioned devices and methods have marked a significant advance in the state of the art of noninvasive blood constituent analysis, one possible source of error arises due to the nature of the contact between these devices and the patient's skin. The above-mentioned U.S. Pat. No. 6,198,949 discloses a spectrometer for noninvasive transfer of thermal gradient spectra to and from living tissue. The spectrometer includes an infrared transmissive thermal mass, referred to as a thermal mass window, for inducing a transient temperature gradient in the tissue by means of conductive heat transfer with the tissue, and a cooling system in operative combination with the thermal mass for the cooling thereof. Also provided is an infrared sensor for detecting infrared emissions from the tissue as the transient temperature gradient progresses into the tissue, and for providing output signals proportional to the detected infrared emissions. A data capture system is provided for sampling the output signals received from the infrared sensor as the transient temperature gradient progresses into the tissue. The transient thermal gradients arising due to the intermittent heating and cooling of the patient's skin generate thermal spectra which yield very good measurements of the patient's blood glucose levels.

Although the apparatus taught in the above-mentioned U.S. Pat. No. 6,198,949 has led to a significant advance in the state of the art of noninvasive blood glucose analysis, one possible source of error arises due to the nature of the contact between the thermal mass window and the patient's skin. If several separate measurements are required, it follows that the thermal mass window must be brought into contact with the patient's skin several times. The problem with this is that each of such contacts tends to be slightly different. For instance, slight differences in pressure or skin topology may arise at the interface between the thermal mass window and the skin; the patient may move that portion of his or her body, for instance the arm, which is in contact with the thermal mass window; and muscular tension may change between measurements. Each of these factors, and perhaps others as well, tend to complicate the already complex nature of the contact between the skin and the thermal mass window.

A device and method are provided for use with a noninvasive optical measurement system, such as a thermal gradient spectrometer, for improved determination of analyte concentrations within living tissue. In one embodiment, a wearable window is secured to a patient's forearm thereby isolating a measurement site on the patient's skin for determination of blood glucose levels. The wearable window effectively replaces a window of the thermal gradient spectrometer, and thus forms an interface between the patient's skin and a thermal mass window of the spectrometer. When the spectrometer must be temporarily removed from the patient's skin, such as to allow the patient mobility, the wearable window is left secured to the forearm so as to maintain a consistent measurement site on the skin. When the spectrometer is later reattached to the patient, the wearable window will again form an interface between the spectrometer and the same location of skin as before.

One embodiment provides a device for use with a noninvasive optical measurement system for capturing thermal spectra from living tissue. The device comprises a window holder and a window connected to the window holder. The window comprises a material of high thermal conductivity so as to permit thermal spectra to pass through the window. The device defines a skin contact surface configured for placement in intimate thermal contact with the skin of a patient. The device further defines a system contact surface opposite the skin contact surface. The system contact surface is configured for removable placement against the noninvasive optical measurement system.

Another embodiment provides a device for consistently interfacing a noninvasive optical measurement system with a location of skin on a patient for capturing thermal spectra therefrom. The device comprises a window holder having an aperture, a window covering the aperture on the window holder, and a heating element disposed upon the window. The window comprises a material of high thermal conductivity so as to permit thermal spectra to pass through the window. The heating element comprises a grid structure which includes a plurality of bridging sub-busses, a plurality of heating wires, and at least two busses disposed on opposite sides of the heating element. The busses comprise an electrical connection whereby electrical communication is established between the heating element and a power supply. The power supply is in operative communication with a timed switching device which intermittently supplies electrical power to the heating element via the electrical connection.

In another embodiment, a method is provided for interfacing a noninvasive optical measurement system with skin of a patient for capturing thermal spectra therefrom. A wearable window is mounted onto the skin of the patient. The wearable window comprises a window holder having an aperture, a window covering the aperture and a heating element disposed upon the window. The window comprises a material of high thermal conductivity so as to permit thermal spectra to pass through the window. An electrical connection is established between the heating element and a power source, and the noninvasive optical measurement system is placed in intimate thermal contact with the window.

In still another embodiment, an apparatus is provided for use with a noninvasive optical measurement system for capturing thermal spectra from living tissue. The apparatus comprises a wearable window which comprises a window holder having an aperture, a window covering the aperture, and a heating element disposed upon the window. The window comprises a material of high thermal conductivity so as to permit thermal spectra to pass through the window. A first electrical connection comprises at least two contacts molded into the surface of the window holder. The contacts are in electrical communication with the heating element. An interface surface of the noninvasive optical measurement system includes a window aperture. The window aperture permits thermal spectra to pass through the interface surface. A second electrical connection comprises at least two pins. Each pin is slidably retained within a socket of the interface surface and spring biased in a protruded state relative to the interface surface. The pins are in electrical communication with a power supply. Pressing the wearable window against the interface surface pushes the pins into the sockets while urging the pins against the contacts.

Another embodiment provides a method for interfacing a noninvasive optical measurement system with skin of a patient. A wearable window is provided. The wearable window comprises a window holder having an aperture, a window covering the aperture, and a heating element disposed upon the window. The window comprises a material of high thermal conductivity so as to permit thermal spectra to pass through the window. The wearable window is mounted onto the skin of the patient such that the heating element is placed into intimate contact with the skin of the patient. Pressure between the wearable window and the skin of the patient causes the window holder to grip the skin, thereby minimizing relative motion between the skin and the wearable window. The wearable window is positioned on an interface surface of the noninvasive optical measurement system such that a window aperture within the interface surface is centered and aligned with the aperture within the window holder. The window aperture permits thermal spectra to pass through the interface surface. An electrical connection is established between the heating element and a power source. The electrical connection comprises a first set of contacts on the surface of the window holder and a second set of contacts on the interface surface. The first set of contacts is in electrical communication with the heating element, and the second set of contacts is in electrical communication with the power source. Pressing the wearable window against the interface surface places the first set of contacts in electrical contact with the second set of contacts.

DETAILED DESCRIPTION OF THE PREFERRED EMBODIMENT

Preferred embodiments of the invention are described below. While the description sets forth various embodiments and specific details, it will be appreciated that the description is illustrative only and should not to be construed in any way as limiting the invention. Furthermore, various applications of the invention, and modifications thereof, which may occur to those skilled in the art, are also encompassed by the general concepts described below.

Figure 1:
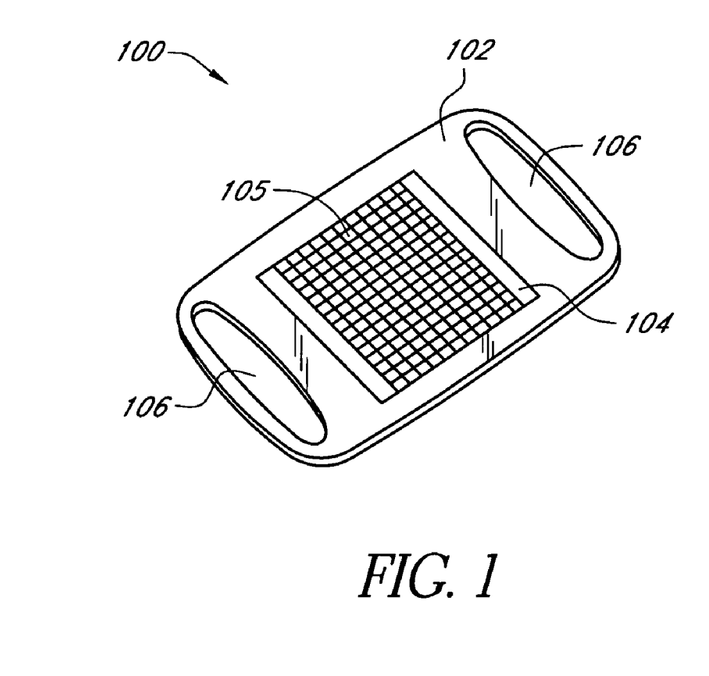
FIG. 1 is a perspective view of one embodiment of a wearable window.

FIG. 1 is a perspective view of one embodiment of a wearable window 100. It is contemplated that the wearable window 100 is to be used in conjunction with a noninvasive optical measurement system such as, but not necessarily limited to, the apparatus taught in the above-mentioned U.S. Pat. No. 6,198,949. This patent discloses a noninvasive thermal gradient spectrometer comprising a window and a, thermal mass window, wherein the window forms an interface between a thermal mass window and a patient's skin. It is contemplated that the wearable window 100 effectively takes the place of the window, and thus forms the interface between the thermal mass window and the patient's skin. It is further contemplated that the wearable window 100 may be used in conjunction with the noninvasive thermal gradient spectrometer in accordance with the methodology taught in the above-mentioned U.S. Pat. No. 6,161,028.

Figure 2:
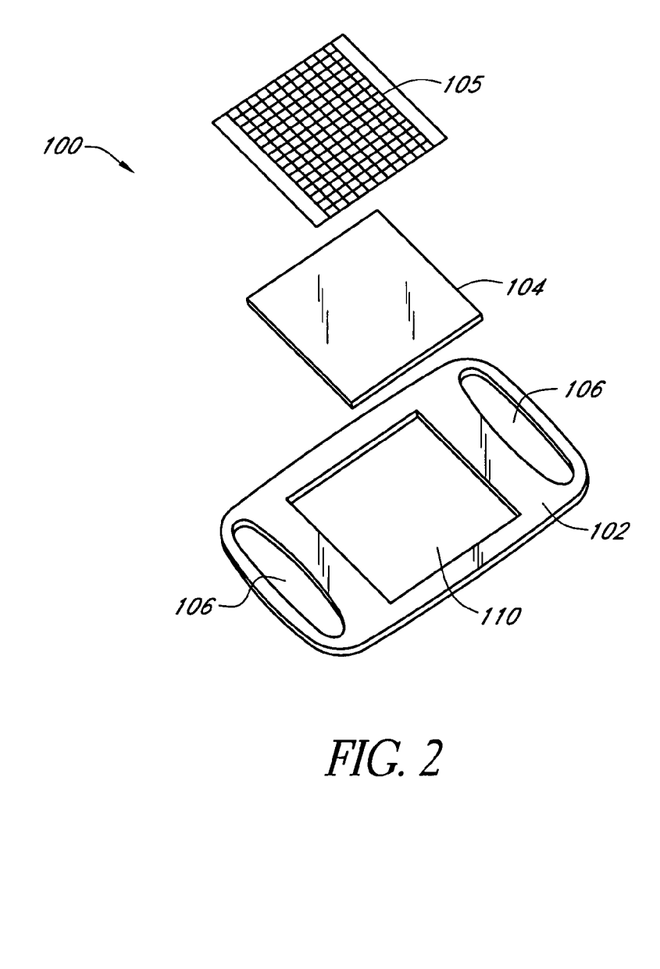
FIG. 2 is an exploded view of the wearable window of FIG. 1.
Figure 4:
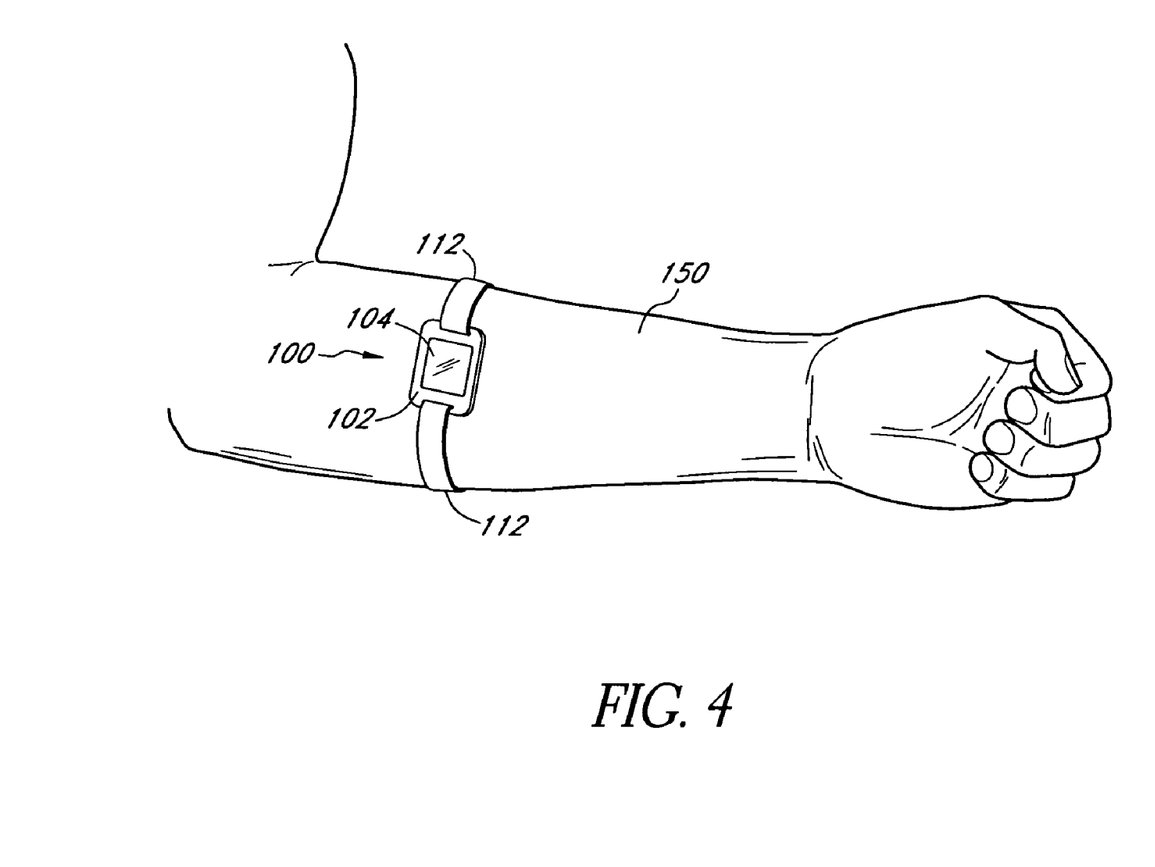
FIG. 4 shows the wearable window of FIG. 1 strapped onto a forearm of a patient.

In the embodiment illustrated in FIG. 1, the wearable window 100 comprises a window holder 102, a substrate 104, a heating element 105, and openings 106 to facilitate fastening the wearable window 100 to a patient (see FIG. 4). FIG. 2 is an exploded view of the wearable window 100, which illustrates the several elements comprising the wearable window 100. As can be seen most clearly in FIG. 2, the window holder 102 serves as a foundation upon which the several elements comprising the wearable window 100 may advantageously be affixed. Furthermore, the window holder 102 serves to facilitate attaching the wearable window 100 to a patient's skin such that the wearable window 100 assumes intimate contact therewith (see FIG. 4).

As used herein, "wearable window" is a broad term and is used in its ordinary sense and refers, without limitation, to anything capable of interfacing with a location on the body as needed for operation of the noninvasive thermal gradient spectrometer. Thus, it is to be noted that the invention need not be limited to the embodiment(s) shown/described herein. The location on the body may comprise a mechanically isolated area of the skin or a landmark such as, by way of example, drawn, printed or tattooed indicia. Furthermore, the wearable window 100 and/or the substrate 104 need not be attachable to the body for prolonged periods of time; e.g., the substrate 104 can alternatively be built into a watch, a ring, an elbow strap which places the substrate 104 in contact with the forearm, or any other similar device which provides a consistent measurement site on the body for operation of the noninvasive thermal gradient spectrometer. Additional information on noninvasive spectrometers and methods may be found in Applicant's copending U.S. patent application Ser. No. 10/200,384, entitled REAGENT-LESS WHOLE-BLOOD GLUCOSE METER, filed Jul. 19, 2002. Additional information about devices and methods for isolating regions of the body may be found in Applicant's copending U.S. patent application Ser. No. 09/970,021, entitled DEVICE FOR ISOLATING REGIONS OF LIVING TISSUE, filed Oct. 2, 2001. The entire contents of each of the above-mentioned patent applications are hereby incorporated by reference herein and made a part of this specification.

The window holder 102 may be formed of injection-molded plastic or other similar material such that the several elements comprising the wearable window 100 may be affixed to the window holder 102 with minimal movement arising therebetween. It is further contemplated that the material comprising the window holder 102 may be such that condensation formed thereon when the window holder 102 is exposed to cooler temperatures (below the dew point) is substantially minimized.

As illustrated in FIG. 2, the window holder 102 further comprises an aperture 110. The aperture 110 allows unimpeded transmission of thermal spectra through the window holder 102 to and from the patient's skin. Although in the embodiment of FIG. 2 the aperture 110 has a rectangular cross-sectional shape, it is contemplated that the aperture 110 may have other cross-sectional shapes, such as, by way of example, square, circular, diamond, elliptical, and ovoid. It is further contemplated that different cross-sectional shapes may advantageously be combined, thereby forming additional cross-sectional shapes.

Disposed upon the aperture 110 of the window holder 102 is the substrate 104. In one embodiment, the substrate 104 has a length and a width that are somewhat greater than the length and width of the aperture 110, thereby facilitating fastening of the substrate 104 to the window holder 102. In another embodiment, the substrate 104 is permanently affixed to the window holder 102. In still another embodiment, the substrate 104 may be removably attached to the window holder 102. In yet another embodiment, the substrate 104 may comprise a disposable member which is attachable to and detachable from the window holder 102.

Alternatively, the substrate 104 may be mounted within the aperture 110 of the window holder 102 such that the upper and lower surfaces of the substrate 104 are flush with upper and lower the surfaces of the window holder 102. In one embodiment, the substrate 104 may be permanently affixed to the perimeter of the aperture 110. In another embodiment, the substrate 104 may be removably attached within the aperture 110. In still another embodiment, the substrate 104 may comprise a disposable member which is attachable to and detachable from within the aperture 110. As will be appreciated by those skilled in the art, the length and width of the substrate 104 are differentially smaller than the length and width of the aperture 110, respectively, such that the substrate 104 may be inserted within the aperture 110. As will be further appreciated, the differentials in the lengths and widths of the substrate 104 and the aperture 110 will depend, in large part, on the materials used for the substrate 104 and the aperture 110, and on the degree to which these materials expand and contract when exposed to a particular temperature range contemplated.

In one embodiment, the substrate 104 is made of a material having a high thermal conductivity, such as polycrystalline float zone silicon or other similar material, such that the substrate 104 is substantially transparent to thermal spectra. In addition, the substrate 104 may have a thickness sized such that thermal spectra are substantially unimpeded as they transfer through the substrate 104. In the illustrated embodiment of FIGS. 1 and 2, the substrate 104 has a thickness of about 0.25 millimeters. It will be appreciated by those of ordinary skill in the art, however, that the material comprising the substrate 104, as well as the dimensions thereof, may advantageously vary from the preferred dimensions as needed.

Figure 2A:
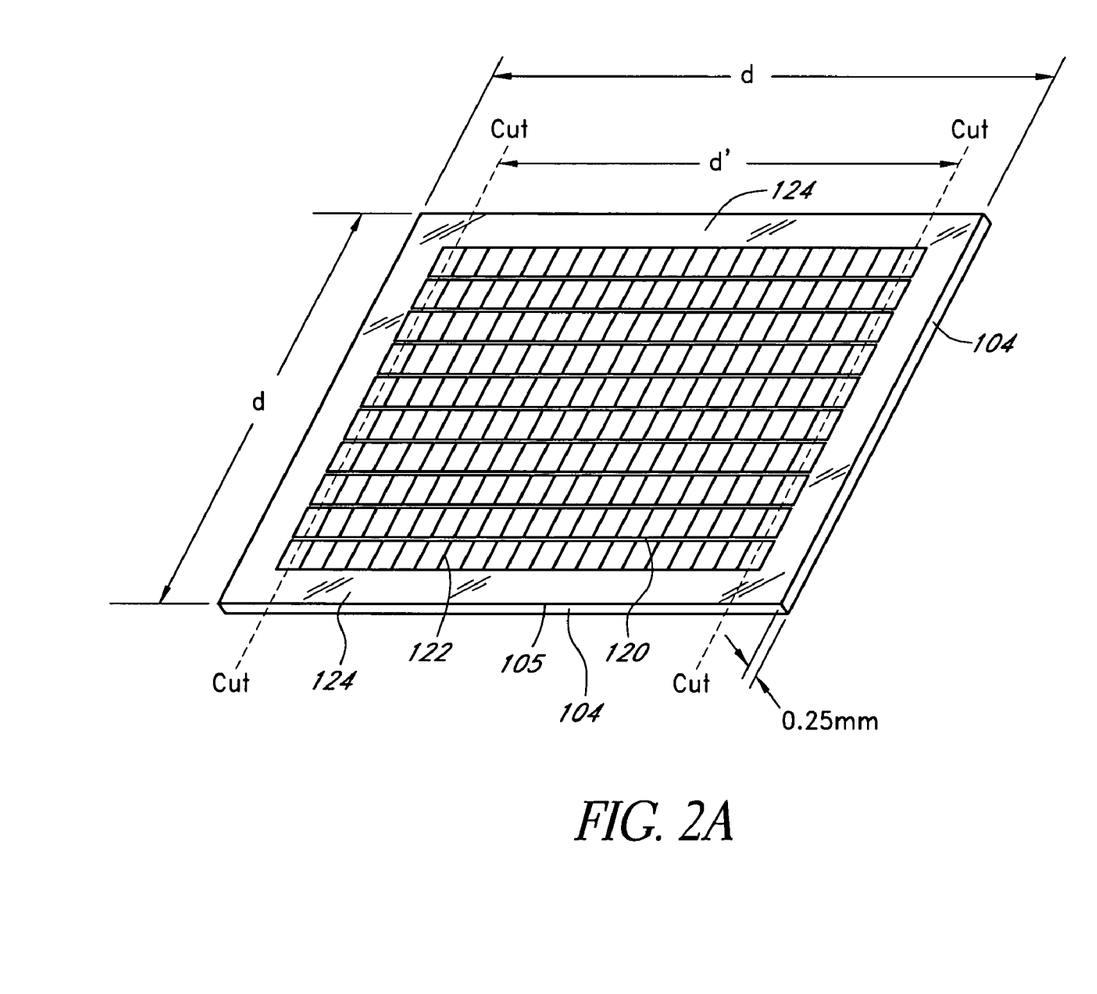
FIG. 2A is a perspective view of an embodiment of a heating element affixed to a substrate.

Disposed upon the substrate 104 is the heating element 105. The heating element 105 transfers heat to the skin of the patient, and thus gives rise to the heating component of the aforementioned intermittent heating and cooling of the patient's skin. Referring to FIG. 2A, the heating element 105 is shown affixed to the substrate 104. The heating element 105 preferably comprises a first adhesion layer of gold or platinum (hereinafter referred to as the "gold" layer) deposited over an alloy layer which is applied to the substrate 104. The alloy layer comprises a material suitable for implementation of the heating element 105, such as, by way of example, 10/90 titanium/tungsten, titanium/platinum, nickel/chromium, or other similar material. The gold layer preferably has a thickness of about 4000 Å, and the alloy layer preferably has a thickness ranging between about 300 Å and about 500 Å. The gold layer and/or the alloy layer may be deposited onto the substrate 104 by chemical deposition including, but not necessarily limited to, vapor deposition, liquid deposition, plating, laminating, casting, sintering, or other forming or deposition methodologies well known to those or ordinary skill in the art.

Once the heating element 105 has been deposited onto the substrate 104, as described above, the heating element 105 is formed into a grid structure comprising a plurality of bridging sub-busses 120, a plurality of heating wires 122, and at least two busses 124. The grid structure of the heating element 105 may be formed by masking, chemical etching, photo etching, ion etching or milling, abrasive etching, grinding or other material forming or removal methodology well known to those of ordinary skill in the art. In one embodiment, the gold and alloy layers comprising the heating element 105 are etched such that the plurality of bridging sub-busses 120 and the plurality of heating wires 122 are formed within the heating element 105. The sub-busses 120 preferably are about 50 $\mu$m wide and spaced by about 1.0 millimeters on center. Furthermore, the heating wires 122 preferably are about 20 $\mu$m wide and spaced by about 0.5 millimeters on center. A person of ordinary skill in the art will recognize that the dimensions and spacing of the bridging sub-busses 120 and the heating wires 122 may vary from the preferred dimensions as needed.

The busses 124 are in electrical communication with a switched power supply (not shown). It is contemplated that the power supply is further in operative communication with a timed switching device or system control (again, not shown) which intermittently supplies electrical power to the heating element 105 via the busses 124. This intermittent application of electrical power may be periodic or aperiodic in nature.

As is further illustrated in FIG. 2A, the substrate 104 and the heating element 105 initially comprise a square having sides of a length d. In one embodiment, the length d is equal to about 12 millimeters. Following the material deposition and etching processes discussed above, the substrate 104 and the heating element 105 are trimmed on two opposing sides such that the two busses 124 are formed on opposite sides of the heating element 105. Trimming of the substrate 104 and the heating element 105 is accomplished by cutting along the lines illustrated in FIG. 2A, which forms a rectangle having dimensions d by d'. In one embodiment, suitable for use with the thermal gradient spectrometer taught in the aforementioned U.S. Pat. No. 6,198,949, d by d' are equal to about 12 millimeters and about 10 millimeters, respectively. However, it will be apparent to those of ordinary skill in the art that alternative alloys, coatings, dimensions, geometries, spacings and bus configurations may advantageously be implemented without detracting from the invention.

It will be appreciated by a person skilled in the art that the heating element 105 may comprise a grid structure (including the bridging sub-busses 120, the heating wires 122, and the busses 124) which is formed as the material is being deposited onto the surface of the substrate 104 by use of a mask or other known techniques. It is contemplated that such an embodiment of the heating element 105 may comprise materials, dimensions, and thermal properties which are substantially the same as those mentioned above.

As will be further appreciated by a person skilled in the art, in an alternative embodiment, the heating element 105 may be omitted from the wearable window 100. It is contemplated that with this embodiment, the wearable window 100 comprises the window holder 102 and the substrate 104, while an element similar in function to the heating element 105 is provided by the thermal gradient spectrometer or other optical measurement system with which the wearable window 100 is intended to be used. It is further contemplated that this embodiment of the wearable window 100 would be particularly useful with thermal gradient spectrometers wherein a heat source has been omitted. In such instances, heating of the patient's skin is accomplished by allowing the skin to warm up naturally to the ambient temperature of the surrounding environment.

Figure 3:
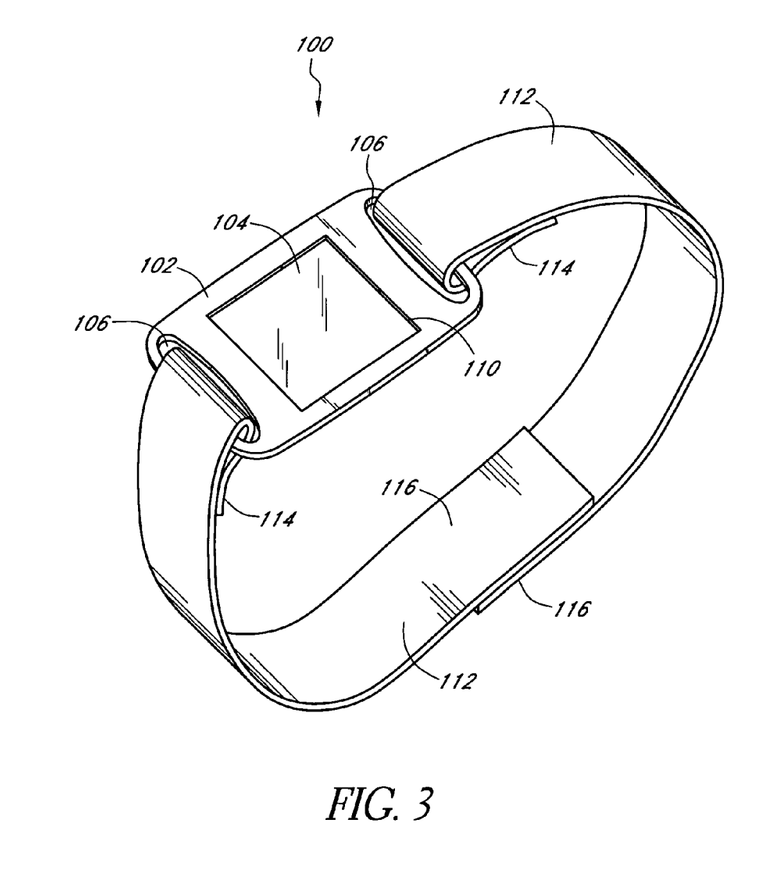
FIG. 3 is a perspective view of the wearable window of FIG. 1 with an attached fastening strap.

FIG. 3 is a perspective view illustrating the wearable window 100 with one embodiment of a fastening strap 112 that may be used in conjunction with the wearable window 100. In the illustrated embodiment, the fastening strap 112 comprises two fixed ends 114 and two adjustable ends 116. Each fixed end 114 passes through one of the openings 106 and then is folded back and affixed to the strap 112 such that the strap is attached to opposite ends of the wearable window 100. The adjustable ends 116 are removably attachable to one another, thereby facilitating fastening of the wearable window 100 onto the patient (see FIG. 4), as well as subsequent removal therefrom. The adjustable ends 116 preferably include strips of Velcro™ (not shown) or other similar material which facilitates repeated attaching and separating of the adjustable ends 116.

A person of ordinary skill in the art will recognize that other techniques may advantageously be utilized for placing the wearable window 100 in contact with the patient's skin. For example, in another embodiment the window holder 102 may include an adhesive material which is adapted to attach the wearable window 100 to the predetermined location on the patient. With this embodiment, the window holder 102 includes a pressure sensitive adhesive surface which enables attaching the wearable window 100 to the patient's skin without using the fastening strap 112.

FIG. 4 generally illustrates the use of an embodiment of the wearable window 100, wherein the wearable window 100 is strapped to a forearm 150 of the patient. As is illustrated, the wearable window 100 is strapped to the forearm 150 such that the heating element 105 is pressed against the patient's skin, while the substrate 104 faces outward away from the skin. Pressure between the wearable window 100 and the patient's skin causes the window holder 102 to "grip" the skin, thereby substantially minimizing relative motion between the skin and the wearable window 100. This gripping of the skin provides location stability whereby the wearable window 100 is prevented from sliding across the patient's skin when pushed or otherwise acted on by external forces, such as forces arising when the noninvasive optical measurement system is coupled to and uncoupled from the wearable window 100.

As will be apparent to those of ordinary skill in the art, the wearable window 100 covers up a region of the skin surrounding the portion of skin from which thermal spectral readings are taken, and prevents moisture evaporation from the covered region of skin. This preserves and stabilizes the hydration level within the region of skin from which readings are taken and is believed to reduce variance and error observed in repeated measurements over time.

In operation, the heating element 105 is placed into electrical communication with a switched power supply (not shown) under the control of the thermal gradient spectrometer or other optical measurement system, whereby intermittent heating is applied to the skin. The spectrometer or other system is placed in thermal contact with the substrate 104 such that the substrate 104 and the heating element 105 together form an interface between the spectrometer and the patient's skin. If, for some reason, the spectrometer must be temporarily removed from thermal/optical contact with the patient's skin, such as to allow the patient mobility, the wearable window 100 may be left strapped to the forearm 150 so as to maintain a consistent measurement site on the skin. When the spectrometer is later reattached to or again placed into thermal contact with the substrate 104, the wearable window 100 will again form an interface between the spectrometer and the same location of skin as before. This substantially reduces measurement errors arising due to variance in the location of the contact between the spectrometer and the patient's skin.

It is to be understood that the wearable window 100 is not restricted to use solely with the forearm 150. For example, the wearable window 100 may advantageously be attached to the end of an index finger. Still, one wearable window 100 may be attached to the index finger while a second somewhat larger wearable window 100 is at the same time attached to the forearm 150, thereby allowing for comparison of measured values. It will be appreciated by those of ordinary skill in the art that the wearable window 100 may advantageously be placed in intimate contact with any location of skin whereupon satisfactory measurements are obtained.

Figure 5:
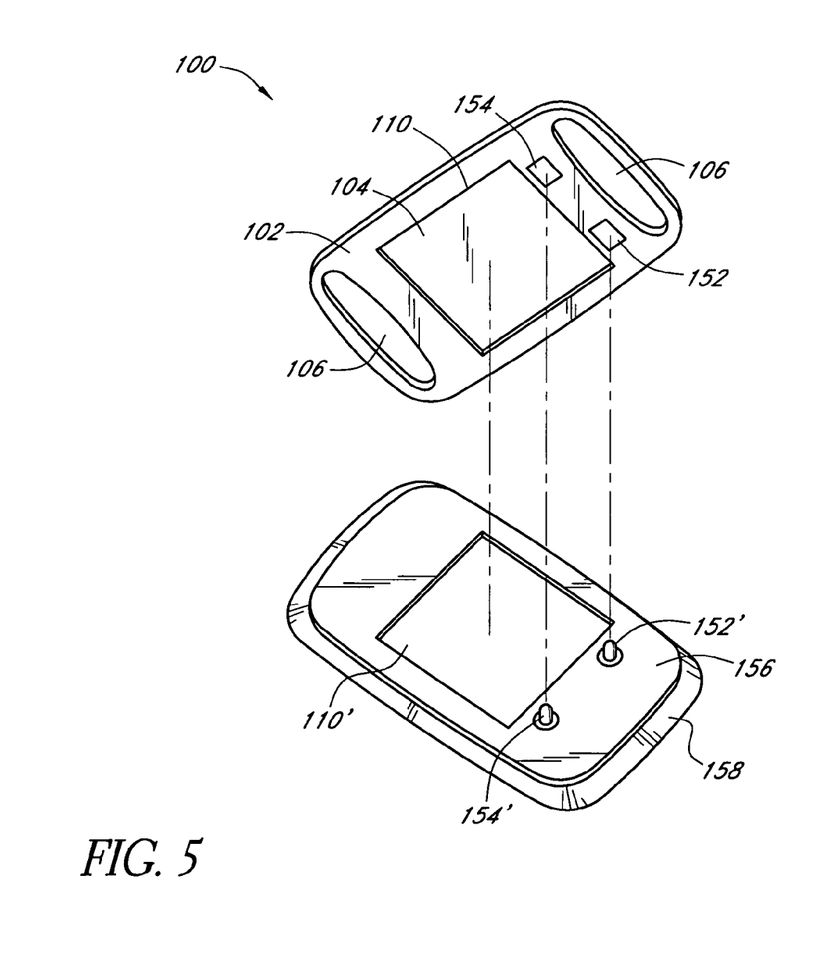
FIG. 5 illustrates one embodiment of an electrical connection established between the wearable window of FIG. 1 and an optical measurement system.

FIG. 5 illustrates one embodiment of an electrical connection established between the wearable window 100 and an optical measurement system 158, whereby electrical power may advantageously be supplied to the heating element 105. In the embodiment illustrated in FIG. 5, the wearable window 100 comprises a first contact 152 and a second contact 154. The contacts 152, 154 are made of an electrically conducting material, such as gold, silver, copper, steel, brass, or other similar material, which is molded into the material comprising the window holder 102. It is contemplated that the contacts 152, 154 are in electrical communication with the heating element 105 (see FIGS. 1 through 3).

As shown, the first contact 152 directly corresponds with a first pin 152' protruding from an interface surface 156 of the optical measurement system 158. Similarly, the second contact 154 directly corresponds with a second pin 154' protruding from the interface surface 156. The pins 152', 154' are slidably retained within sockets (not shown) and are spring biased such that they are in a neutral, protruded state relative to the interface surface 156. When the wearable window 100 is pressed against the interface surface 156, the pins 152', 154' are pushed into the sockets while being urged against the contacts 152, 154. It is contemplated that the pins 152', 154' are made of an electrically conducting material, such as gold, silver, copper, steel, brass, or other similar material, and are in electrical communication with a switched power supply (not shown) which resides on the optical measurement system 158 or externally thereto. Alternatively, an electrical connection may be established between the optical measurement system 158 and the heating element 105 by the use of electrical wires (not shown). It is contemplated that a "power cord" comprising electrical wires may be passed directly from the switched power supply to the heating element 105, thereby obviating the pins 152', 154' and the sockets on the interface surface 156, as well as the contacts 152, 154 on the window holder 102.

The interface surface 156 may be made of rubber or other semi-compliant material which grips the wearable window 100, thereby preventing relative motion between the wearable window 100 and the optical measurement system 158. The interface surface 156 includes an aperture 110' which directly corresponds with the aperture 110 of the wearable window 100. The aperture 110' allows thermal spectra unimpeded passage between the wearable window 100 and the optical measurement system 158.

As shown in the embodiment of FIG. 5, the interface surface 156 has a thickness which provides a thin layer of airspace between a window (not shown) of the optical measurement system 158 and the substrate 104. In another embodiment, however, the substrate 104 may have a thickness such that when the wearable window 100 is pressed against the interface surface 156, a portion of the substrate 104 extends through the aperture 110' and comes into thermal contact with the window of the optical measurement system 158.

In operation, the wearable window 100 is fastened to the skin of a patient and then is pressed against the interface surface 156 such that the apertures 110, 110' are centered and aligned, and electrical communication is respectively established between the pins 152', 154' and the contacts 152, 154. As the wearable window 100 is further pressed onto the interface surface 156, the pins 152', 154' and the contacts 152, 154 remain in electrical communication as the pins are pushed into their respective sockets.

Once the wearable window 100 is sufficiently pressed against the interface surface 156, the heating element 105 is placed into electrical communication with the above-mentioned switched power supply (not shown), whereby intermittent heating is applied to the skin. The optical measurement system 158 is placed in thermal contact with the substrate 104 such that the substrate 104 and the heating element 105 together form an interface between the optical measurement system 158 and the patient's skin.

Although preferred embodiments of the invention have been described in detail, certain variations and modifications will be apparent to those skilled in the art, including embodiments that do not provide all of the features and benefits described herein. Accordingly, the scope of the invention is not to be limited by the illustrations or the foregoing descriptions thereof.

What is claimed is:

1. A device for use with a noninvasive optical measurement system for capturing thermal spectra from living tissue, said device comprising:
    a window holder; and
    a window connected to said window holder, said window comprising a material of high thermal conductivity so as to permit thermal spectra to pass through said window;
    said device defining a skin contact surface configured for placement in intimate thermal contact with the skin of a patient;
    said device further defining a system contact surface opposite said skin contact surface; said system contact surface being configured for removable placement against said noninvasive optical measurement system;
    further comprising a heating element disposed upon said window;
    wherein said heating element comprises a grid structure.

2. The device of claim 1, wherein said window holder has an aperture allowing unimpeded transmission of thermal spectra through said window holder.

3. The device of claim 1, wherein said window holder is made of injection-molded plastic.

4. The device of claim 1, wherein said material is polycrystalline float zone silicon.

5. The device of claim 1, wherein said material has a thickness of about 0.25 millimeters.

6. The device of claim 1, wherein said grid structure comprises a plurality of bridging sub-busses spaced apart from one another and a plurality of heating wires spaced apart from one another, and at least two busses disposed on opposite sides of said heating grid.

7. The device of claim 6, wherein said sub-busses each has a width of about 50 micrometers.

8. The device of claim 6, wherein said sub-busses are spaced apart from one another by about 1.0 millimeters on center.

9. The device of claim 6, wherein said heating wires each has a width of about 20 micrometers.

10. The device of claim 6, wherein said busses comprise an electrical connection whereby electrical communication is established between said heating element and a power supply.

11. The device of claim 10, wherein said power supply is in operative communication with a timed switching device which intermittently supplies electrical power to said heating element via said electrical connection.

12. A device for use with a noninvasive optical measurement system for capturing thermal spectra from living tissue, said device comprising:
    a window holder; and
    a window connected to said window holder, said window comprising a material of high thermal conductivity so as to permit thermal spectra to pass through said window;

said device defining a skin contact surface configured for placement in intimate thermal contact with the skin of a patient;

said device further defining a system contact surface opposite said skin contact surface; said system contact surface being configured for removable placement against said noninvasive optical measurement system;

further comprising a heating element disposed upon said window, said heating element comprising a grid structure which in turn comprises a plurality of bridging sub-busses spaced apart from one another and a plurality of heating wires spaced apart from one another, and at least two busses disposed on opposite sides of said heating element;

wherein said heating wires are spaced apart from one another by about 0.5 millimeters on center.

13. A device for consistently interfacing a noninvasive optical measurement system with a location of skin on a patient for capturing thermal spectra therefrom, said device comprising:

a window holder having an aperture;

a window covering said aperture on said window holder, said window comprising a material of high thermal conductivity so as to permit thermal spectra to pass through said window; and a heating element disposed upon said window, said heating element comprising a grid structure which includes a plurality of bridging sub-busses, a plurality of heating wires, and at least two busses disposed on opposite sides of said heating element.

14. The device of claim 13, wherein said device defines a skin contact surface configured for placement in intimate thermal contact with said predetermined location of skin on the patient, said device further defining a system contact surface opposite said skin contact surface; said system contact surface being configured for removable placement against said noninvasive optical measurement system.

15. The device of claim 13, wherein said sub-busses each has a width of about 50 micrometers.

16. The device of claim 13, wherein said sub-busses are spaced apart from one another by about 1.0 millimeters on center.

17. The device of claim 13, wherein said heating wires each has a width of about 20 micrometers.

18. The device of claim 13, wherein said heating wires are spaced apart from one another by about 0.5 millimeters on center.

19. The device of claim 13, wherein said busses comprise an electrical connection whereby electrical communication is established between said heating element and a power supply.

20. The device of claim 19, wherein said power supply is in operative communication with a timed switching device which intermittently supplies electrical power to said heating element via said electrical connection.

21. The device of claim 13, wherein said heating element comprises a gold layer deposited over an alloy layer which is affixed to said window, said gold layer and said alloy layer being formed into said grid structure.

22. The device of claim 21, wherein said gold layer has a thickness of about 4000 Angstroms.

23. The device of claim 21, wherein said alloy layer has a thickness ranging between about 300 Angstroms and about 500 Angstroms.

24. The device of claim 13, wherein said window holder is made of injection-molded plastic.

25. The device of claim 13, wherein said material is polycrystalline float zone silicon.

26. The device of claim 13, wherein said window has a thickness of about 0.25 millimeters.

27. An apparatus for use with a noninvasive optical measurement system, said apparatus comprising:

a wearable window comprising a window holder having an aperture, a substrate covering said aperture, said substrate comprising a material of high thermal conductivity, and a heating element disposed upon said substrate;

a first electrical connection comprising at least two contacts on the surface of said window holder, said contacts being in electrical communication with said heating element;

an interface surface of said noninvasive optical measurement system, said interface surface including a window aperture; and a second electrical connection comprising at least two pins, projections biased towards a protruded state relative to said interface surface, said projections being in electrical communication with a power supply;

wherein pressing said wearable window against said interface surface surges said projections away from said protruded state while urging said projections against said contacts.

28. The apparatus of claim 27, wherein said projections each corresponds with one of said contacts so as to form a closed circuit between said power supply and said heating element when said wearable window is pressed against said interface surface of said noninvasive optical measurement system.

29. The apparatus of claim 27, wherein said contacts are made of an electrically conducting material.

30. The apparatus of claim 27, wherein said window aperture directly corresponds with said aperture within said window holder.

31. The apparatus of claim 27, wherein said window aperture permits thermal spectra to pass through said interface surface.

32. The apparatus of claim 27, wherein said interface surface is made of a semi-compliant material which grips said wearable window so as to minimize relative motion therebetween.

33. The apparatus of claim 32, wherein said semi-compliant material is rubber.

34. The apparatus of claim 27, wherein pressure between said wearable window and the skin of the patient causes said window holder to grip the skin, thereby minimizing relative motion between the skin and the wearable window.

35. The apparatus of claim 27, wherein said power supply is in operational communication with a timed switching device whereby electrical power is intermittently applied to said heating element.

36. A method for interfacing a noninvasive optical measurement system with skin of a patient, said method comprising:

providing a wearable window comprising a window holder having an aperture, a substrate covering said aperture, said substrate comprising a material of high thermal conductivity, and a heating element disposed upon said substrate;

mounting said wearable window onto the skin of the patient such that said heating element is placed into thermal communication with the skin of the patient;

positioning said wearable window on an interface surface of said noninvasive optical measurement system such that a window aperture within said interface surface is centered and aligned with said aperture within the window holder; and establishing an electrical connection between said heating element and a power source;

wherein said electrical connection comprises a first set of contacts on the surface of said window holder and a second set of contacts on said interface surface, said first set of contacts being in electrical communication with said heating element, said second set of contacts being in electrical communication with said power source, wherein pressing said wearable window against said interface surface places said first set of contacts in electrical contact with said second set of contacts.

37. The method of claim 36, wherein pressure between said wearable window and the skin of the patient causes said window holder to grip the skin, thereby minimizing relative motion between the skin and said wearable window.

38. The method of claim 36, wherein said window aperture permits thermal spectra to pass through said interface surface.

39. The method of claim 36, wherein said power source supplies electrical power intermittently to said heating element.

40. The method of claim 36, wherein said second set of contacts comprises at least two pins each slidably retained within a socket of said interface surface and spring biased in a protruded state relative to said interface surface.

* * * * *

UNITED STATES PATENT AND TRADEMARK OFFICE
CERTIFICATE OF CORRECTION

PATENT NO. : 6,959,211 B2 Page 1 of 1
APPLICATION NO. : 10/213730
DATED : October 25, 2005
INVENTOR(S) : Rule et al.

It is certified that error appears in the above-identified patent and that said Letters Patent is hereby corrected as shown below:

TITLE PG. ITEM (56) PG 2 COL 2 after "6,198,949" delete "B1" and insert -- A --, therefor.

In Column 1, Line 41 delete "SOLD-STATE" and insert -- SOLID STATE --, therefor.

In Column 4, Line 45, delete "a," and insert -- a --, therefor.

In Column 11, Line 33, Claim 14, delete "predetennined" and insert -- predetermined --, therefor.

In Column 12, Line 20, Claim 27, before "projections" delete "pins,".

In Column 12, Line 24, Claim 27, delete "surges" and insert -- urges --, therefor.

Signed and Sealed this

Third Day of October, 2006

JON W. DUDAS
*Director of the United States Patent and Trademark Office*